United States Patent
Leininger et al.

(10) Patent No.: US 11,725,221 B2
(45) Date of Patent: Aug. 15, 2023

(54) METHODS FOR IMPROVING YIELDS OF A POLYUNSATURATED FATTY ACID (PUFA) OIL CONTAINING PRODUCT USING MULTIPLE CENTRIFUGATION STEPS

(71) Applicants: DSM IP Assets B.V., Heerlen (NL); Evonik Operations GMBH, Essen (DE)

(72) Inventors: Neil Francis Leininger, Columbia, MD (US); Holger Pfeifer, Hanau-Wolfgang (DE); David Allen Tinsley, Columbia, MD (US); Jochen Lebert, Hanau-Wolfgang (DE); Marc Beiser, Hanau-Wolfgang (DE)

(73) Assignees: DSM IP ASSETS B.V., Heerlen (NL); EVONIK OPERATIONS GMBH, Essen (DE)

(*) Notice: Subject to any disclaimer, the term of this patent is extended or adjusted under 35 U.S.C. 154(b) by 381 days.

(21) Appl. No.: 16/636,940

(22) PCT Filed: Aug. 9, 2018

(86) PCT No.: PCT/US2018/046081
§ 371 (c)(1),
(2) Date: Feb. 6, 2020

(87) PCT Pub. No.: WO2019/032880
PCT Pub. Date: Feb. 14, 2019

(65) Prior Publication Data
US 2020/0362373 A1  Nov. 19, 2020

Related U.S. Application Data

(60) Provisional application No. 62/543,659, filed on Aug. 10, 2017.

(51) Int. Cl.
*C12P 7/6472* (2022.01)
*A23L 33/12* (2016.01)
*A23D 9/04* (2006.01)
*B01D 21/26* (2006.01)
*C11B 1/10* (2006.01)

(52) U.S. Cl.
CPC ............ *C12P 7/6472* (2013.01); *A23D 9/04* (2013.01); *A23L 33/12* (2016.08); *B01D 21/262* (2013.01); *C11B 1/10* (2013.01); *A23V 2002/00* (2013.01)

(58) Field of Classification Search
None
See application file for complete search history.

(56) References Cited

U.S. PATENT DOCUMENTS

| | | |
|---|---|---|
| 2011/0159167 A1 | 6/2011 | Ruesing et al. |
| 2011/0177031 A1* | 7/2011 | Apt .................. A23K 50/00 435/243 |
| 2014/0073037 A1* | 3/2014 | Patinier .................. C11B 1/04 435/267 |
| 2015/0159116 A1* | 6/2015 | Patinier ............. A23L 33/115 554/205 |
| 2016/0319217 A1 | 11/2016 | Triplett et al. |
| 2017/0002383 A1 | 1/2017 | Kawai Shikishima |

FOREIGN PATENT DOCUMENTS

| | | |
|---|---|---|
| EP | 1178118 A1 | 2/2002 |
| EP | 2145942 A1 | 1/2010 |
| WO | 2015095694 A1 | 6/2015 |

OTHER PUBLICATIONS

International Search Report issued in International Application No. PCT/US2018/046081, dated Oct. 11, 2018 (3 pages).
Supplementary European Search Report issued by the European Patent Office in European Application No. 18844409, dated Mar. 31, 2021 (10 pages).

\* cited by examiner

*Primary Examiner* — Christian L Fronda
(74) *Attorney, Agent, or Firm* — Nixon & Vanderhye P.C.

(57) ABSTRACT

This invention relates to a method of using a two-step serial centrifugation process in extracting nutritive oil from a fermentation broth, this novel method prevents oil yield losses while preserving product quality.

12 Claims, 2 Drawing Sheets

METHODS FOR IMPROVING YIELDS OF A POLYUNSATURATED FATTY ACID (PUFA) OIL CONTAINING PRODUCT USING MULTIPLE CENTRIFUGATION STEPS

CROSS-REFERENCE TO RELATED APPLICATIONS

This application is a National Stage of International Application No. PCT/US2018/046081 filed Aug. 9, 2018, and which claims the benefit of the filing date of U.S. Provisional Patent Application No. 62/543,659 filed Aug. 10, 2017, the entire contents of each of which are hereby incorporated herein by reference in their entireties.

BACKGROUND OF THE INVENTION

Nutritive Oils are becoming well recognized as necessary for inclusion in a daily diet to achieve various desirable health effects. One genus of such nutritive oils is polyunsaturated fatty acid containing oils (PUFAs). The sources of these types of oils are manifold and include fish, microbial (yeast and algal), and possible genetically modified plants. It is also well known that, due to the desirable unsaturation, these oils are readily oxidizable and, thereby, sensitive to heat and extensive process times. If these oils do oxidize, the oxidation byproduct has an extremely bad taste and the product is avoided by consumers. Further, it is desirable to use continuous or semi-continuous manufacturing processes to reduce production cost. The semi-continuous manufacturing process here refers to the batch wise processing of fermentation media at the end of fermentation process. The continuous manufacturing process here refers to continuous processing of fermentation media, with continuous replenishing of the fermentation media that has been processed. The challenge with continuous or semi-continuous manufacturing processes, however, is to bring all the process steps into a reasonable time frame, allowing a continuous or semi-continuous process to be used. One of the major sub processes during a continuous or semi-continuous manufacturing process is the isolation and purification of the desirable oils after they have been extracted from the oil-generating microbes that have been fermented and then lysed in order to maximize oil yield.

Isolating and purifying these types of oils is challenging since the oils are intended for human consumption and so the generation of oxidation byproducts must be minimized and the usage of certain toxic additives to facilitate the isolation and purification of these oils must be avoided.

Methods for isolating and purifying these types of oils are known and, in many of them, after fermentation and cell lysis, there is typically an aqueous removal step of the oil product for the purposes of product separation and purification. During the aqueous removal step, it is typical to separate the aqueous phase from the oil phase and isolating the desirable oil end-product while removing cellular debris, digestion enzymes, and other process aids. Making an exact separation at the interface of two immiscible fluids is complicated, however, by the presence of a stable emulsion which is due to the natural emulsifiers created by the fermented microbes and released during digestion and cell wall rupture. Either a problem of yield loss or a problem of poor yield will arise.

In order to enhance oil yield, extra steps on the part of oil manufacturer have been tried. However, it will substantially add to the cost of the final product. Further, given the sensitivity of the nutritive oils to oxidation, addition of extra processing steps will result in the oxidation of the desirable oils. Such oxidized oil product produces a very undesirable odor as perceived by the user.

What is needed, but presumably lacking, is a manufacturing process that will deliver product yields of greater than that of the existing method, while still minimizing further oxidation of the final oil product and do not compromise oil quality. Considering the extremely large volumes of product manufactured, every yield improvement such as at increment of 1% will generate substantial cost savings in the manufacture of nutritive oils.

SUMMARY OF THE INVENTION

By using a two-step serial centrifugation process, the dilemma of choosing between taking oil with high quality but losing on oil yield and taking oil with high yield but losing on oil quality is avoided.

In a traditional single step centrifugation process, the final oil product is collected from the light phase after one centrifugation step. Either an oil with high quality oil is collected or an oil with high yield is collected, but not both. For example, if high quality oil is desired, the separation cut will be made into the light phase and thus away from the interface between light phase and heavy phase. This leaves out some of the oil-containing fluid to be discarded together with the heavy phase product, resulting in loss of oil yield. If high oil yield is desired, the separation cut will be made into the heavy phase close to the interface of the light phase and heavy phase in order to collect as much oil as possible. Oil collected by such method includes impurities in the isolated oil and thus jeopardizes oil quality.

The two-step serial centrifugation process helps to resolve the above problem. After the first centrifugation step, the separation cut is made into the heavy phase close to the interface of the light phase. Maximal amount of oil in the light phase is retained and thus high oil yield is ensured. The oil collected from the first centrifugation process, high in oil yield but low in oil quality, is transferred to a second centrifuge. After the second centrifugation, high quality oil is obtained by making the separation cut into the light phase and away from the interface of the light phase and heavy phase. The oil yield is also improved by recycling the heavy phase product from the second centrifugation into the next batch of fermentation broth which is ready to be processed. The oil-rich recycled product described above further enhances demulsification in the next batch of fermentation broth. The technique disclosed in this invention prevents yield losses while preserves product quality.

In one embodiment, the invention is directed to a method of improving nutritive oil product yield, wherein the method comprises performing at least two centrifugation steps on a fermentation broth.

In an embodiment of the above method, the light phase product produced after the first centrifugation step is fed into the centrifuge of the second centrifugation step, and the heavy phase product produced after the first centrifugation step is discarded. In separating the resulting light phase and heavy phase from the first centrifugation step, the separation cut is made into the heavy phase side and is close to the interface of the light phase and heavy phase in order to collect as much as oil as possible.

In a further embodiment of the above method, the light phase product produced after the second centrifugation step is retained and the heavy phase product produced after the second centrifugation step is recycled to a fermentation broth which will be processed in the next round of processing using the above two centrifugation steps. In separating the resulting light phase and heavy phase from the second centrifugation, the separation cut is made into the light phase side and is close to the interface between light phase and heavy phase, in order to avoid collecting impurities from the heavy phase.

In one embodiment, the nutritive oil is polyunsaturated fatty acid (PUFA) oil.

In another embodiment, the yield of the nutritive oil product is greater than 88%, 92%, or even 95%.

DETAILED DESCRIPTION OF THE INVENTION

Figure 1:
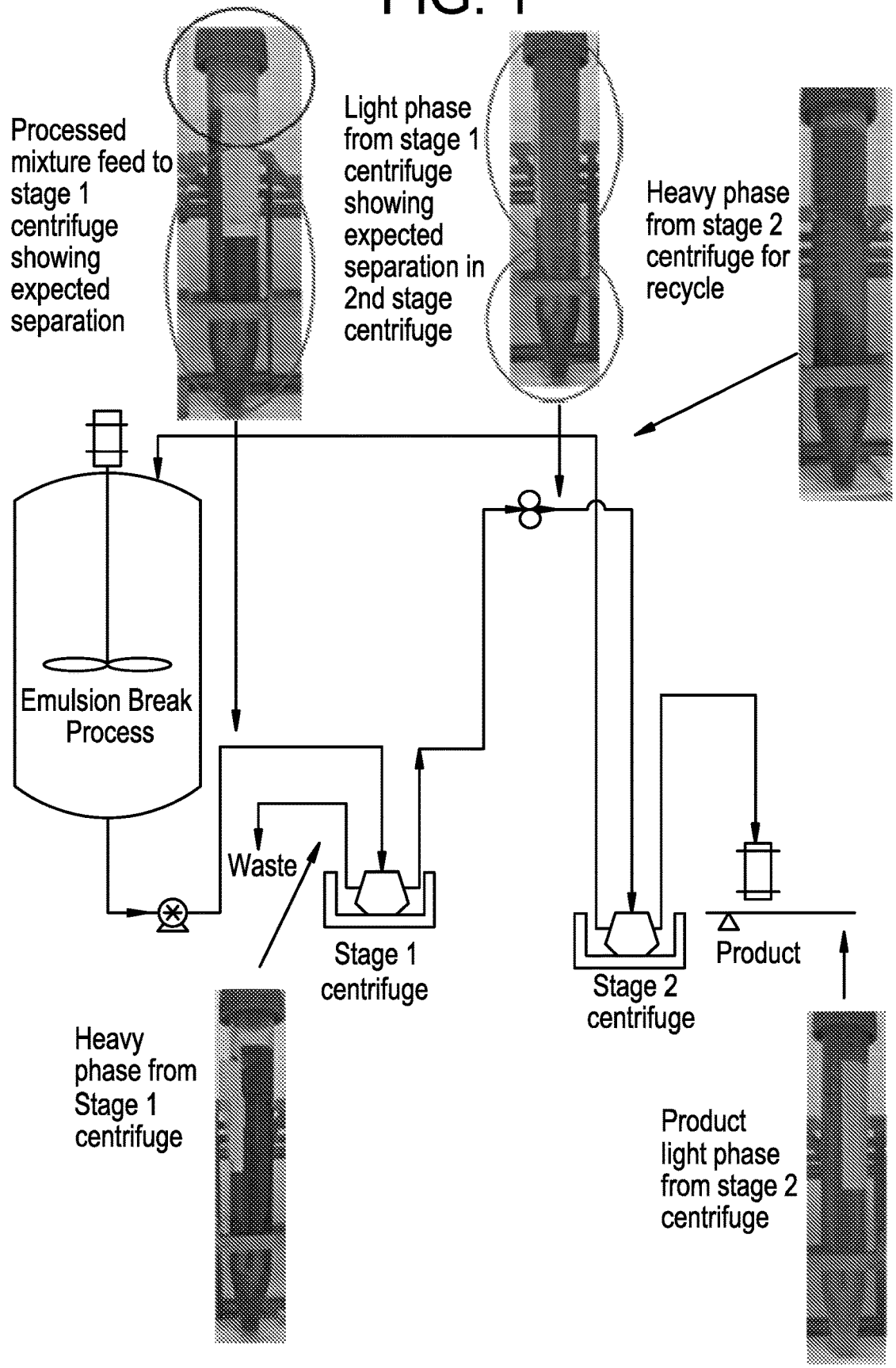
FIG. 1 is schematic illustration of the double centrifugation process disclosed in the present application.

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well-known and commonly employed in the art.

The features and advantages of the invention may be more readily understood by those of ordinary skill in the art upon reading the following detailed description. It is to be appreciated that certain features of the invention that are, for clarity reasons, described above and below in the context of separate embodiments, may also be combined into subcombinations thereof.

Embodiments identified herein as exemplary are intended to be illustrative and not limiting.

In this specification and in the claims that follow, reference will be made to a number of terms, which shall be defined to have the following meanings:

The use of the terms "a" and "an" and "the" and similar referents in the context of describing the invention (especially in the context of the following claims) are to be construed to cover both the singular and the plural, unless otherwise indicated herein or clearly contradicted by context.

The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

"Optional" or "optionally" means that the subsequently described event or circumstance can or cannot occur, and that the description includes instances where the event or circumstance occurs and instances where it does not.

An "oil", as used herein, refers to nutritive oils. In one embodiment, it refers to PUFA oil.

"Aqueous" as used herein, refers to either water alone or water combined with other water-soluble components that are included to enhance the product of facilitate the product manufacturing process.

An "oil phase" as used herein, refers to the portion of an aqueous/oil mixture that is oil soluble.

"Aqueous phase" as used herein, refers to the portion of an aqueous/oil mixture that is water soluble.

"Light phase" or "light phase product" as used herein, refers to the upper portion of a centrifugation product. It is a solution with light color because it mainly contains oil. It is also called oil phase in this application.

"Heavy phase" or "heavy phase product" as used herein, refers to the lower portion of a centrifugation product. It is a solution or sludge with dark color because it mainly contains cellular debris. It is also called aqueous phase in this application because it is water soluble.

"Fermentation broth" as used herein, refers to the medium in which the microbial organisms that produce the desirable oils is grown.

"Emulsifiers" as used herein, refers to ingredients that are naturally produced by the oil producing microbes that cause an emulsion to form between the aqueous and organic phases of the fermentation broth.

"Two centrifugation steps" as used herein, refers to a process for extracting nutritive oil, wherein two centrifugation steps are performed before the final oil product is retained. This phrase is used interchangeably in this application with the phrase "double centrifugation", both of which share the same meaning.

In the present invention, as demonstrated in FIG. 1, two or more centrifugation steps are conducted in a process of isolating nutritive oil product from a fermentation broth. During the first step centrifugation, a light phase and a heavy phase are formed. In order to maximize oil yield, the separation is made into the heavy phase and thus the light phase along with a small amount of the unwanted heavy phase are collected. The rest of unwanted aqueous phase is discarded. The product collected from the first centrifugation is then fed into a second step centrifuge which again separates the product into a light phase and a heavy phase. The high-quality oil is collected from the light phase. The heavy phase and together with a small amount of light phase, is recycled to the next batch of fermentation broth for further treatment to break the emulsion and subsequent extraction of oil. Alternatively, the heavy phase and a portion of light phase is treated in further processing steps to break emulsion.

In one embodiment, non-limiting examples of nutritive oils are unsaturated fatty acids such as EPA, DHA, ARA, and DPA.

In one embodiment, non-limiting examples of heavy phase components are water, salts, fatty acids, cell debris, and other ionic materials.

With the teachings herein, it is to be understood that a person of ordinary skill in the art can adjust these processes to provide desired effects such as process speed, purity, yield and the like and, as such, it is contemplated that multiple process steps not expressly defined herein but could be made routinely based on the disclosure above are considered as part of this teaching.

In a specific embodiment, a double centrifugation process is contemplated. This embodiment can be summarized thusly:

Weigh the aqueous/oil mixture into a heating vessel having an agitator selected from the group of axial flow or radial flow impellers and any combination of these.

a. Adding a fermentation broth to a vessel;
b. Adding components to facilitate the breaking of emulsion formation
c. Heating the vessel;
d. Pumping the fermentation broth to a first centrifuge;
e. Centrifuging the mixture in a continuous process and discarding the heavy phase;
f. Pumping the remaining mixture into a second centrifuge;
g. Centrifuging the mixture;
h. Retaining the oil product in the new light phase in step g and recycling the new heavy phase and remaining light phase by pumping back to the vessel in step a) where a new round of fermentation broth is added.

In one embodiment, the vessel in step c is heated to at least 70° C.

It is contemplated that the double centrifugation method described in this application can be used both in a bath process where the fermentation broth in the emulsion breaking vessel is emptied before the next batch of fermentation broth is added, and in a semi-continuous process where new fermentation broth is continuously added to the emulsion breaking vessel as the broth is consumed by the centrifugation processes. Thus, in one embodiment, steps a) to h) are performed in batches. In another embodiment, steps a) to h) are performed continuously.

In one embodiment, in step c) the vessel is heated to at least 40° C., at least 50° C., at least 60° C., at least 70° C., at least 75° C., at least 80° C., at least 85° C., at least 90° C., or at least 95° C.

In another embodiment, the manufacturing methods are modified to be made in liquid processing equipment that is specifically designed for centrifugation processes involving liquids. An example is the BD series of Alfa Laval Centrifuges. <Ref:http://www.alfalaval.com/products/separation/centrifugal-separators/separators/BD-series/>. Adjustments are made to the manufacturing embodiments disclosed herein according to the equipment manufacturer's instructions and the knowhow that a person having ordinary skill would have after receiving the teachings herein.

In another embodiment, the two stage centrifugation process is used in any fermentation broth process wherein the oil product is physically and chemically separated from the biomeal and the oil is immiscible with the biomeal.

In one embodiment, the method of extracting nutritive oil using two centrifugation steps is repeated one more time. In another embodiment, the method is repeated two more time. In yet another embodiment, the method is repeated three time.

In some embodiments, the oil yield is greater than 88%, 89%, 90%, 91%, 92%, 93%, 94%, or 95%.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments and preferred ranges may be interchanged either in whole or in part and/or be combined in any manners. Therefore, the spirit and scope of the appended claims should not be limited to the description of the preferred versions contained therein.

Calculation of Oil Yield

The yields can be calculated by two methods. The first method would be preferred in a production environment where accounting would require understanding all losses, including process losses and transfer losses. The second method would be preferred in a laboratory or pilot environment where focus is on the process losses only.

Method 1—Overall Mass Balance

The fraction of oil contained in the product stream from the $2^{nd}$ centrifuge is measured through standard analytical methods, such as FAME. The resulting fraction is multiplied by the total mass of the product stream. This result is then divided by the fraction of oil in the feed mixture as measured by analytical methods multiplied by the total mass of the feed mixture. The result is multiplied by 100 to provide a % Yield.

Method 2—Calculation of Yield from Losses

The fraction of oil in the heavy phase and in the shots from the $1^{st}$ centrifuge is assumed to be the only process loss. This fraction of oil in the heavy phase and the shots is measured by standard analytical methods such as FAME. The resulting fraction of oil in the heavy phase from the $1^{st}$ centrifuge is multiplied by the total mass of the heavy phase. The resulting fraction of oil in the shots from the $1^{st}$ centrifuge is multiplied by the total mass of the shots. These results are added together and divided by the fraction of oil in the centrifuge feed stream, measured through standard analytical methods such as FAME, multiplied by the sum of the streams leaving the $1^{st}$ centrifuge; namely the light phase, the heavy phase, and the shots. The result is the fraction of oil loss in the process. This number is subtracted from 1 and the result is multiplied by 100 to give the % yield.

EXAMPLES

Example 1

In this example, the equipment set-up of the present invention is described. The following example is from AEX-O-753 as found in Table 1. 2400 kg of broth which was a mixture of cellular materials, oil, water, and other fermentation required compounds, and which included an intermediate emulsion layer, was contained in a 3000-liter vessel which provided adequate mixing to make the mixture nearly homogeneous. The mixture in this vessel was fed to a disk stack centrifuge using a pump and control loop for flow. The centrifuge was fed at a rate of 6 liter/min, and was adjusted to separate the mixture into three parts, one part being the heavy aqueous phase, one part being high solids from the bowl shot, and the other part being the light oil phase. The proportion of these phases 1 part light phase/4.5 part heavy phase/0.04 shot. The separation in the centrifuge was controlled to a setpoint of 10% moisture in the light phase, and actually resulted in approximately 9% moisture in the light phase. Approximately 95% of the oil and any intermediate layer was contained in the light phase. The moisture in the light phase as determined by typical moisture analysis on heated scale moisture analyzer could be controlled to approximately 10%+/−3%. The light phase from the $1^{st}$ separation was a mixture of approximately 85% oil, 9% water, and 6% other aqueous mixture.

This mixture was fed to a $2^{nd}$ disk stack centrifuge. The light phase from this $1^{st}$ separation was captured in a 55 gallon drum and fed to a 100 liter vessel with adequate mixing to maintain homogeneity. This mixture from the $1^{st}$ separation was separated by the second separation into two phases, a light phase and a heavy phase. The proportions of the phases were 72% light phase and 28% heavy phase. The setup of the $2^{nd}$ centrifuge was that the light phase would be almost entirely oil containing less than 1%, or even less than 0.5%, moisture. The actual moisture in the light phase was 0.4%. The heavy phase contained the intermediate emulsion layer from the original mixture and almost all the water. The heavy phase also contained approximately 85% oil. The heavy phase from the $2^{nd}$ centrifuge was recycled to the next batch of fermentation broth for further treatment.

The yield, based on losses from the $1^{st}$ centrifuge heavy phase, was calculated to be 95.5%, using Method 2 as the method to calculate yields.

Example 2

In this example, the equipment described in Example 1 was used to extract nutritive oil by performing a single centrifugation was performed. Sample 3 shows the oil yield after two rounds of double centrifugation was performed. In making Sample 3, the heavy phase product from the first round of double centrifugation was recycled to the fermentation broth which was subsequently processed in the second round of double centrifugation.

The data in Table 1 demonstrated that the double centrifugation method described in this application causes higher oil yield than single centrifugation method. The data in Table 1 further demonstrated that by recycling the heavy phase mixture produced from the second centrifugation to the fermentation broth to be used for the next round of processing further increase the oil yield.

Further analysis of oil quality shows no variation among Samples #1-5.

TABLE 1

| | Product Yield % for comparative samples | | | | |
|---|---|---|---|---|---|
| Sample # | 1 (AEX-O-709) | 2 (AEX-O-710) | 3 (AEX-O-740) | 4 (AEX-O-741) | 5 (AEX-O-753) |
| Round of centrifugation | 1 round of Single centrifugation | 1 round of double centrifugation | 2 rounds of double centrifugation | 3 rounds of double centrifugation | 4 rounds of double centrifugation |
| Yield (%) | 87.1 | 89.8 | 95.6 | 93.0 | 95.5 | centrifugation step, or by preforming the two centrifugation steps as contemplated by the present invention, or by performing one or more repeats of the two centrifugation steps.

Oil samples obtained after performing the above oil extraction process are obtained and compared to show the advantage of the present invention.

Sample 1 was the PUFA oil obtained from a fermentation broth after performing a single centrifugation step. This represents the comparative example.

Sample 2 was the PUFA oil obtained from a fermentation broth after performing a two centrifugation steps.

Sample 3 was the PUFA oil obtained from a fermentation broth after performing a two centrifugation steps and is followed by one more round of two centrifugation steps. The discarded mixture from the second centrifugation step of the previous round of double centrifugation is added to the fermentation broth of the next rounds of double centrifugation.

Sample 4 was the PUFA oil obtained from a fermentation broth after performing a two centrifugation steps and is followed by two more round of two centrifugation steps. The discarded mixture from the second centrifugation step of the previous round of double centrifugation is added to the fermentation broth of the next rounds of double centrifugation.

Sample 5 was the PUFA oil obtained from a fermentation broth after performing a two centrifugation steps and is followed by three more round of two centrifugation steps. The discarded mixture from the second centrifugation step of the previous round of double centrifugation is added to the fermentation broth of the next rounds of double centrifugation.

Figure 2:
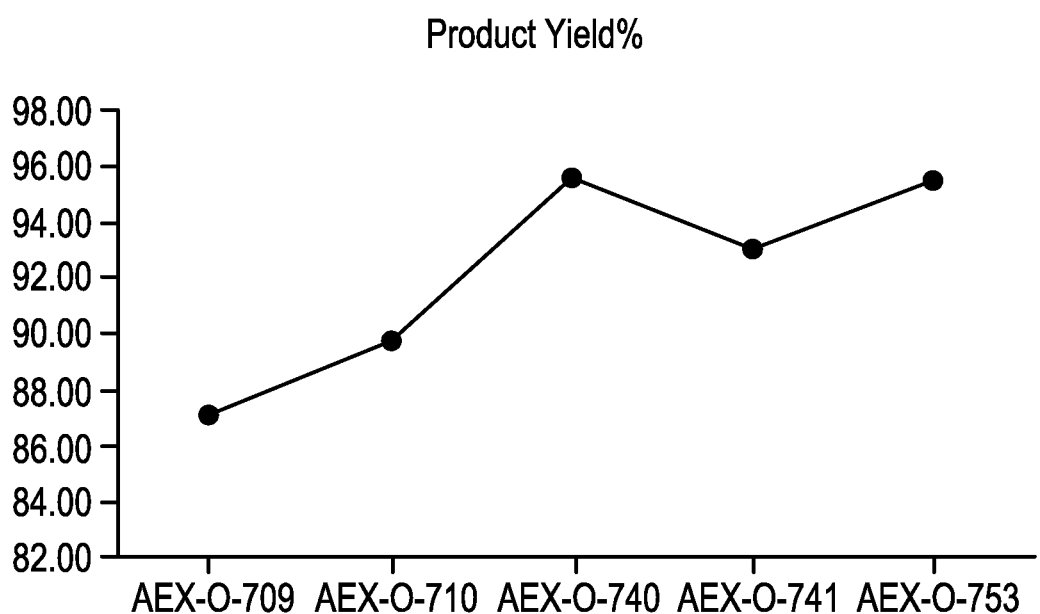
FIG. 2 is the graphical depiction of the data in Table 1, which compares the oil yield % among samples prepared with different rounds of centrifugations.

The advantage of a method of using two centrifugation steps over the conventional method of using a single centrifugation step is shown Table 1 and also graphically in FIG. 2. Sample 1 is the comparative sample which shows the result of a single centrifugation step. The heavy phase product in sample 1 was discarded instead of being recycled. Sample 2 shows the oil yield after one round of double

What is claimed is:

1. A method of improving product yield of a polyunsaturated fatty acid (PUFA) oil containing product, wherein the method comprises:

(a) directing a PUFA oil-containing fermentation broth to a first centrifuge and subjecting the PUFA oil-containing fermentation broth to a first centrifugation step within the first centrifuge to form a first centrifuged product comprised of a first light phase and a first heavy phase;

(b) separating the first light phase from the first heavy phase in the first centrifuged product by making a first separation cut of the first centrifuged product into the first heavy phase below an interface between the first light phase and the first heavy phase thereof;

(c) discarding the first heavy phase separated from the first centrifuged product and directing the first light phase separated from the first centrifuged product to a second centrifuge;

(d) subjecting the first light phase separated from the first centrifuged product to a second centrifugation step in the second centrifuge to form a second centrifuged product comprised of a second light phase and a second heavy phase;

(e) separating the second light phase from the second heavy phase in the second centrifuged product by making a second separation cut of the second centrifuged product in the second light phase close to an interface between the second light phase and the second heavy phase thereof;

(f) retaining the second light phase separated from the second centrifuged product and recycling the second heavy phase obtained from the second centrifuged product to fresh PUFA oil-containing fermentation broth to be directed to the first centrifuge.

2. The method of claim 1, wherein the PUFA oil yield of the second light phase is greater than 88%.

3. The method according to claim 1, wherein step (a) comprises the steps of:
- (a1) adding the fermentation broth to a vessel;
- (a2) adding a component to the fermentation broth to facilitate breaking of emulsion formation;
- (a3) heating the vessel; and
- (a4) pumping the fermentation broth to a first centrifuge.

4. The method of claim 3, wherein the component in step (a2) is an enzyme or sodium hydroxide.

5. The method of claim 4, wherein in step (a3) comprises heating the vessel to a temperature selected from the group consisting of at least 40° C., at least 50° C., at least 60° C., at least 70° C., at least 75° C., at least 80° C., at least 85° C., at least 90° C., and at least 95° C.

6. The method of claim 3, wherein PUFA oil yield of the second light phase is greater than 88%.

7. The method of claim 6, wherein PUFA oil yield of the second light phase is greater than 92%.

8. The method of claim 6, wherein PUFA oil yield of the second light phase is greater than 95%.

9. The method according to claim 3, wherein step (c) comprises the step of pumping the first light phase from the first centrifuge into the second centrifuge.

10. The method of claim 1, wherein the process comprises repeating the steps (a)-(f) at least one time.

11. The method of claim 10, wherein the process comprises repeating the steps (a)-(f) two more times.

12. The method of claim 10, wherein the process comprises repeating the steps (a)-(f) three more times.

* * * * *